US011623400B2

(12) United States Patent
Cambron et al.

(10) Patent No.: US 11,623,400 B2
(45) Date of Patent: Apr. 11, 2023

(54) MODULAR LIGHT SOURCE FOR CURING OF 3D PRINTED BIOLOGICAL AND ENGINEERED MATERIALS

(71) Applicant: Advanced Solutions Life Sciences, LLC, Louisville, KY (US)

(72) Inventors: Scott Cambron, Louisville, KY (US); Andrew Davis Blum, Louisville, KY (US)

(73) Assignee: ADVANCED SOLUTIONS LIFE SCIENCES, LLC, Louisville, KY (US)

(*) Notice: Subject to any disclaimer, the term of this patent is extended or adjusted under 35 U.S.C. 154(b) by 67 days.

(21) Appl. No.: 17/166,694

(22) Filed: Feb. 3, 2021

(65) Prior Publication Data
US 2021/0237355 A1 Aug. 5, 2021

Related U.S. Application Data

(60) Provisional application No. 62/969,320, filed on Feb. 3, 2020.

(51) Int. Cl.
*B29C 64/282* (2017.01)
*B29C 64/379* (2017.01)
(Continued)

(52) U.S. Cl.
CPC .......... *B29C 64/282* (2017.08); *B29C 64/379* (2017.08); *B29C 71/04* (2013.01);
(Continued)

(58) Field of Classification Search
CPC ..... B29C 64/282; B29C 64/379; B29C 71/04; B29C 64/118; B29C 64/209;
(Continued)

(56) References Cited

U.S. PATENT DOCUMENTS

| 9,407,837 B2 * | 8/2016 | Lee ................... H04N 9/04559 |
| 2014/0267713 A1 * | 9/2014 | Basque ................... G01N 1/08 |
| | | 901/47 |

(Continued)

FOREIGN PATENT DOCUMENTS

| CN | 109732923 | 5/2019 |
| WO | WO-2020014786 A1 * | 1/2020 |

OTHER PUBLICATIONS

European Patent Office: International Search Report and Written Opinion issued for PCT/US2021/016408 dated May 19, 2021. 16 pages.

*Primary Examiner* — Minh D A
(74) *Attorney, Agent, or Firm* — Gray Ice Higdon

(57) ABSTRACT

A modular light for removably attaching to a bio-printer robot end effector, where the light includes: an annular modular light ring housing with an annular opening for receiving the end effector of the bioprinting robot; the housing substantially surrounding a dispensing tip of the end effector; a power supply interface to receive electrical power from the end effector; a plurality of LEDs positioned annularly around the end effector within the annular modular light ring housing, where the plurality of LEDs are spaced in at least two annular rows, where each of the at least two annular rows are at a unique elevational position within the annular modular light ring housing with respect to a light output plane of the annular modular light ring housing; the LEDs are in electrical communication with the power supply interface; and a controller communicatively coupled with the LEDs and the power supply interface.

22 Claims, 13 Drawing Sheets

(51) Int. Cl.
*H05B 45/20* (2020.01)
*H05B 47/16* (2020.01)
*H05B 45/10* (2020.01)
*B29C 71/04* (2006.01)
*C12N 5/00* (2006.01)
*F21V 21/096* (2006.01)
*B33Y 10/00* (2015.01)
*B33Y 30/00* (2015.01)
*B33Y 80/00* (2015.01)
*F21Y 105/18* (2016.01)
*F21Y 115/10* (2016.01)

(52) U.S. Cl.
CPC .......... *C12N 5/0062* (2013.01); *F21V 21/096* (2013.01); *H05B 45/10* (2020.01); *H05B 45/20* (2020.01); *H05B 47/16* (2020.01); *B33Y 10/00* (2014.12); *B33Y 30/00* (2014.12); *B33Y 80/00* (2014.12); *F21Y 2105/18* (2016.08); *F21Y 2115/10* (2016.08)

(58) Field of Classification Search
CPC ... B29C 64/264; B29C 64/112; C12N 5/0062; F21V 21/096; H05B 45/10; H05B 45/20; H05B 47/16; B33Y 10/00; B33Y 30/00; B33Y 80/00; F21Y 2105/18; F21Y 2115/10; Y02B 20/40
See application file for complete search history.

(56) References Cited

U.S. PATENT DOCUMENTS

| | | |
|---|---|---|
| 2018/0311898 A1 | 11/2018 | Schwarzbaum et al. |
| 2018/0326660 A1 | 11/2018 | Gifford et al. |
| 2019/0118448 A1 | 4/2019 | Selim et al. |
| 2019/0327394 A1* | 10/2019 | Ramirez Luna ....... A61B 34/32 |

\* cited by examiner

MODULAR LIGHT SOURCE FOR CURING OF 3D PRINTED BIOLOGICAL AND ENGINEERED MATERIALS

BACKGROUND

Fabrication of tissue or other constructs through bioprinting may involve challenges related to resolution, compatibility with a range of printable "bioinks", and preserving cell viability throughout the printing process. Crosslinking may address these challenges, as it allows a liquid "bioink" containing cells to be printed, and then following printing be crosslinked or cured. This crosslinking may be the formation of a chemical bond between two polymers, protein chains, or two different parts of the same chain. One way this crosslinking may be achieved is through a photoinitiatior when irradiated with light. Use of light for crosslinking is particular advantageous for bioprinting, as light is minimally invasive and may be controllable on site and on demand by a user.

Many conventional light rings, wands, or the like may be utilized at a robotic end effector (e.g. of a bioprinter). However, these lights, wands, etc. include the limitation that they are typically limited to a single wavelength, thus limiting their use. Furthermore, the mounting of the ring, wand, etc. may alter the exposure profile. As a non-limiting example, a wand mounted to an end effector may result in a non-axisymmetric exposure profile of the dispensing tip. Finally, the conventional ring lights may not be modular.

Figure 1:
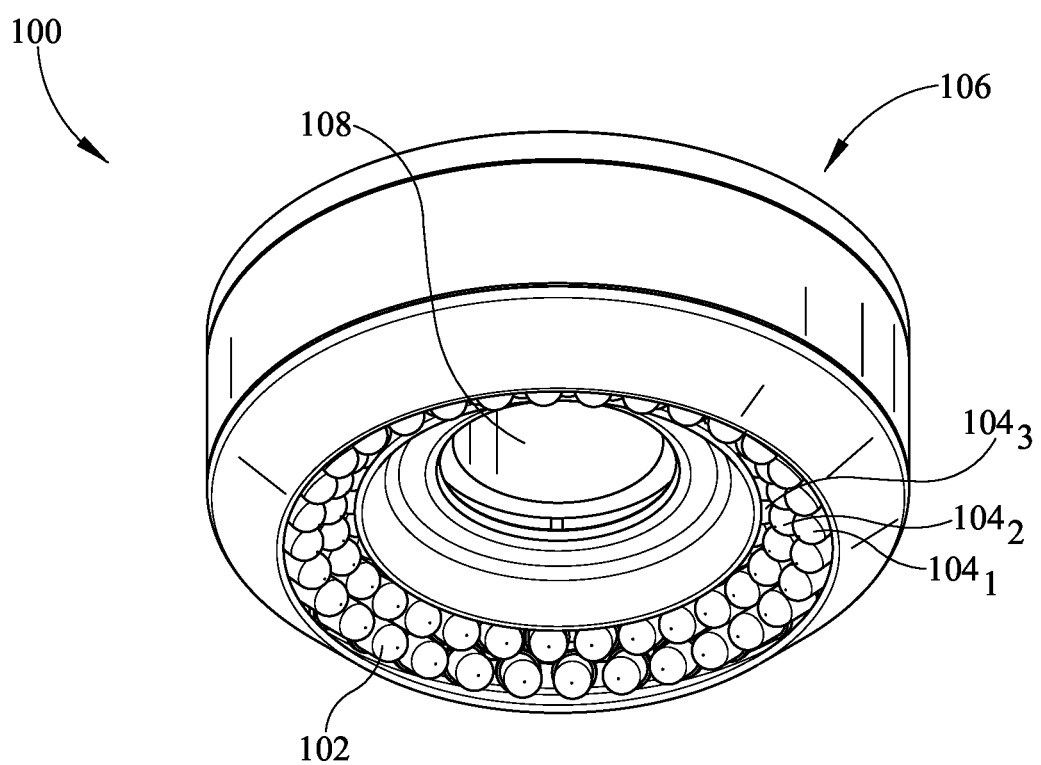
FIG. 1 is a lower perspective view of a modular light ring in accordance with an embodiment described herein.

Before any embodiments are explained in detail, it is to be understood that the various aspects are not limited in its application to the details of construction and the arrangement of components set forth in the following description or illustrated in the following drawings. The embodiments are capable of being practiced or of being carried out in various ways. Also, it is to be understood that the phraseology and terminology used herein is for the purpose of description and should not be regarded as limiting.

SUMMARY OF THE EMBODIMENTS

During bioprinting, a solution of a biomaterial (e.g. a solution of cells of a desired type) is termed a "bioink". This bioink is used in the printing process to generate tissue constructs. The bioink may be crosslinked, stabilized, or cured. This bioink can be crosslinked or stabilized during or immediately after bioprinting to generate the final shape, structure, and architecture of the designed construct.

When a liquid "bioink" is printed the "bioink" may need to be set, cured, etc. to form a tissue construct, for example the formation of a three-dimensional bio-printed cartilage. Crosslinking may address these challenges, as it allows a liquid "bioink" containing cells to be printed, and then during or following printing be crosslinked or cured. When used to described crosslinking in bioprinting, crosslinking may describe the formation of one or more chemical bond between polymers, protein chains, or two different parts of the same chain. In bioprinting, light may be used to achieve crosslinking, one way this crosslinking may be achieved is through the use of light, or photocrosslinking. For example, the bioink may include a gelatin methacryloyl (GelMA) with a photoinitiator such as Irgacure 2959. Light has the advantage of being minimally invasive and may be easily controlled by a user. The application of light allows for crosslinking bioinks with photosensitive cells on demand without a significant reducing in cell viability. The term modular refers to the ability of a light to be easily attached and detached, and ability to fit many differing types of end-effectors. In such an instance, the modular light may be easily removed and replaced in an automated fashion, thus minimizing the risk of introducing contaminants into the environment.

The herein-described embodiments address these and other problems associated with the art by providing a modular light configured to removably attach to a bioprinting robot end effector that includes: an annular modular light ring housing with an annular opening for receiving the end effector of the bioprinting robot; the annular modular light ring housing substantially surrounding a dispensing tip of the bioprinting robot end effector; a power supply interface to receive electrical power from the bioprinting robot end effector; the annular modular light ring housing removably replaceable around the dispensing tip of the bioprinting robot end effector; a plurality of LEDs positioned annularly around the end effector within the annular modular light ring housing, where the plurality of LEDs are spaced in at least two annular rows, where each of said plurality of at least two annular rows are at a unique elevational position within the annular modular light ring housing with respect to a light output plane of the annular modular light ring housing; the plurality of light emitting diodes (LEDs) in electrical communication with the power supply interface; and at least one controller communicatively coupled with the plurality of light emitting diodes and the power supply interface, the controller configured to: receive, from a user interface, one or more light output characteristics; drive the plurality of LEDs defined by the LED row information and the LED sector information, at a frequency to generate the one or more light output characteristics.

In some embodiments the annular modular light ring housing is removably replaceable with at least one magnet adjacent the bioprinting robot end effector and an interfacing magnet in the annular modular light ring housing. In other embodiments, the annular modular light ring housing is removably replaceable with at least one mechanical interface between the bioprinting robot end effector and the annular modular light ring housing. In some embodiments, the power supply interface is an electrical contact configured to electrically connect the end effector and the modular light. In some embodiments, the plurality of light emitting diodes are disposed on a printed circuit board.

In some embodiments, the plurality of light emitting diodes a first and second portion of the plurality of light emitting diodes, where the first and second portions of the plurality of LEDs emit light at a different light output characteristics. In some such embodiments, the first and second portions of the plurality of light emitting diodes are each divided into a plurality of sectors, where each of the plurality of sectors is separately controlled by the controller. In some such embodiments, the controller is further configured to: receive the one or more light output characteristics for at least one of the plurality of sectors from the user interface; and drive at least one of plurality of sectors individually at the one or more light output characteristics by the controller.

In other embodiments, the at least two annular rows of LEDs include a first annular row, a second annular row and a third annular row, where the first annular row of LEDs are elevationally closer to the light output plane than the second annular row and the third annular row. In some such embodiments, the controller is further configured to: receive one or more light output characteristics for at least one of the first, second or third annular rows of LEDs from the user interface; drive one of the first, second or third row of the plurality of rows of LEDs at a first light output characteristics, by the controller; and drive another of the first, second or third row of the plurality of rows of LEDs at a second light output characteristic which is different than the first light output characteristic by the controller.

In some embodiments, the power supply interface of the modular light receives curing data from the bio-printing robot end effector connection. In some embodiments, the user interface received curing data. In some such embodiments, the curing data includes LED segment and wavelength information. In some such embodiments, the LED segment information includes grouping information of the plurality of LEDs, the grouping information defining a plurality of groups of LEDs, each of the plurality of groups having a unique wavelength with respect to the other of the plurality of groups. In some embodiments, the at least one controller includes at least one microprocessor; in some such embodiments, the at least one microprocessor includes a first microprocessor.

In another aspect, a modular light configured to removably attach to a bio-printing robot end effector includes: an annular modular light ring housing with an annular opening configured to receive the end effector of the bio-printing robot, the annular light ring housing having a light emitting plate directed outward away from the end effector in the direction of a dispensing tip of the bioprinting robot; the annular modular light ring housing removably replaceable around the dispensing tip of the bioprinting robot end effector; a power supply interface to receive electrical power; the annular modular light ring housing removably replaceable around the dispensing tip of the bioprinting robot end effector and retained in place on the end effector using a coupling; a plurality of LEDs positioned annularly around the end effector within the modular light ring housing, wherein the plurality of LEDs are spaced in at least two annular rows, wherein each of said plurality of at least two annular rows are individually controllable in unique quadrants; the plurality of light emitting diodes in electrical communication with the power supply interface; a user interface; and at least one controller communicatively coupled with the plurality of light emitting diodes and the power supply interface, the controller configured to: receive curing data including one or more light output characteristics from the user interface; drive a plurality of LEDs defined by the LED row information and the LED sector information, at a frequency to generate the one or more light output characteristics.

In some embodiments, the coupling is a magnet configured to interact with a corresponding magnet of the end effector. In other embodiments, the coupling is a mechanical coupling. In some embodiments, the power supply interface is an electrical contact configured to electrically connect the end effector and the modular light ring. In some embodiments, the first row of the plurality of LEDs generates light at a first intensity and the second row of the plurality of LEDs generates light a second, differing intensity. In other embodiments, the first and second rows of the plurality of LEDs are each divided into a plurality of sectors, where each of the plurality of sectors is separately controlled.

In yet another aspect, a method of configuring a modular light ring including an annular modular light ring housing with an annular opening configured to receive the end effector of the bioprinting robot, a power supply, a plurality of LEDs positioned annularly around the end effector within the modular light ring housing, wherein the plurality of LEDs are spaced in at least two annular rows, where each of the plurality of at least two annular rows are at a unique elevational position within the modular light ring housing with respect to a light output plane of the modular light ring housing, and a controller, the method includes: receiving one or more intensity or irradiance value for at least one of the first or second rows of the plurality of light emitting diodes from a user interface; and driving a plurality of LEDs defined by the LED row information and the LED sector information at a frequency to generate the one or more intensity or irradiance value from a controller.

In some embodiments, the at least two annular rows of LEDs include a first annular row, a second annular row and a third annular row, the first annular row of LEDs are elevationally closer to the light output plane than the second annular row and the third annular row, and the method further includes: receiving one or more light output characteristics for at least one of the first, second or third annular rows of LEDs from the user interface; driving one of the first, second or third row of the plurality of rows of LEDs at a first light output characteristics by the controller; and driving another of the first, second or third row of the plurality of rows of LEDs at a second light output characteristic which is different than the first light output characteristic, by the controller.

DETAILED DESCRIPTION

Bio-printing based solutions often utilize automated processes which include 2 or 3-dimensional bio-printing using various printing materials. These bio-printers have become significantly automated and incorporate the use of robotic arms having end effectors to complete the intricate bio-printing step. Finalization of the bio-printing process further often requires a step of curing or initiating crosslinking of the bio-printing material. This can be accomplished utilizing illumination techniques at specified wavelengths or duration/exposure time and intensity/irradiance. These illumination characteristics can be controlled but must also be directed at the appropriate location of the bio-printed material to effectuate efficient curing and/or crosslinking of the material.

In various implementations of the modular light source 100 disclosed herein, the modular light ring 100 may be removably replaced at the end effector and controlled by the robotic bio-printing device so that efficient, directed and specific curing and/or crosslinking is effectuated. This can be accomplished by matching not only the illumination output characteristics to the used bio-printing material but also pairing the location of the printed material with required illumination characteristics and coordinated location control of the emitted illumination. Further, such illumination at the end-effector of the bio-printer robotic arm may also be removably replaced with a different modular ring so that different light output characteristics may be readily utilized in the bio-printing process. Such control may be further effectuated utilizing a light ring with has associated on-board electronics to power a plurality of LEDs within the modular light ring 100 but also related controller(s) to drive the LEDs are the necessary wavelength, duration, intensity or other specification requirements paired with the bio-printing ink.

Hence in the bio-printing process, particularly in those which combine with curing/crosslinking implementations that include LED-based light sources, it is desirable to have control over one or more of the light sources. For example, it may be desirable to control which of one or more light sources/LEDs are illuminated and/or to control one or more lighting parameters of one or more of the light sources. For example, it may be desirable to control color, color temperature, intensity, power consumption, beam width, and/or beam direction of light output provided by one or more LED-based light sources of a light emitting device.

As used herein for purposes of the present disclosure, the term "LED" should be understood to include any electroluminescent diode or other type of carrier injection/junction-based system that is capable of generating radiation in response to an electric signal and/or acting as a photodiode. Thus, the term LED includes, but is not limited to, various semiconductor-based structures that emit light in response to current, light emitting polymers, organic light emitting diodes (OLEDs), electroluminescent strips, and the like. In particular, the term LED refers to light emitting diodes of all types (including semi-conductor and organic light emitting diodes) that may be configured to generate radiation in one or more of the infrared spectrum (from about 700 to about 1000 nanometers), ultraviolet spectrum (about 250 to about 400 nanometers), and various portions of the visible spectrum (generally including radiation wavelengths from approximately 400 nanometers to approximately 700 nanometers). Some examples of LEDs include, but are not limited to, various types of infrared LEDs, ultraviolet LEDs, red LEDs, blue LEDs, green LEDs, yellow LEDs, amber LEDs, orange LEDs, and white LEDs (discussed further below). It also should be appreciated that LEDs may be configured and/or controlled to generate radiation having various bandwidths (e.g., full widths at half maximum, or FWHM) for a given spectrum (e.g., narrow bandwidth, broad bandwidth), and a variety of dominant wavelengths within a given general color categorization.

For example, one implementation of an LED configured to generate essentially white light (e.g., a white LED) may include a number of dies which respectively emit different spectra of electroluminescence that, in combination, mix to form essentially white light. In another implementation, a white light LED may be associated with a phosphor material that converts electroluminescence having a first spectrum to a different second spectrum. In one example of this implementation, electroluminescence having a relatively short wavelength and narrow bandwidth spectrum "pumps" the phosphor material, which in turn radiates longer wavelength radiation having a somewhat broader spectrum.

It should also be understood that the term LED does not limit the physical and/or electrical package type of an LED. For example, as discussed above, an LED may refer to a single light emitting device having multiple dies that are configured to respectively emit different spectra of radiation (e.g., that may or may not be individually controllable). Also, an LED may be associated with a phosphor that is considered as an integral part of the LED (e.g., some types of white LEDs). In general, the term LED may refer to packaged LEDs, non-packaged LEDs, surface mount LEDs, chip-on-board LEDs, T-package mount LEDs, radial package LEDs, power package LEDs, LEDs including some type of encasement and/or optical element (e.g., a diffusing lens), etc.

A given light source may be configured to generate electromagnetic radiation within the visible spectrum, outside the visible spectrum, or a combination of both. Hence, the terms "light" and "radiation" are used interchangeably herein. Additionally, a light source may include as an integral component one or more filters (e.g., color filters), lenses, or other optical components. Also, it should be understood that light sources may be configured for a variety of applications, including, but not limited to, indication, display, and/or illumination. An "illumination source" is a light source that is particularly configured to generate radiation having a sufficient intensity to effectively illuminate a target area. In this context, "sufficient intensity" refers to sufficient radiant power in the visible spectrum generated on the target area (the unit "lumens" often is employed to represent the total light output from a light source in all directions, in terms of radiant power or "luminous flux") to provide ambient illumination (i.e., light that may be perceived indirectly and that may be, for example, reflected off of one or more of a variety of intervening surfaces before being perceived in whole or in part).

The term "spectrum" should be understood to refer to any one or more frequencies (or wavelengths) of radiation produced by one or more light sources. Accordingly, the term "spectrum" refers to frequencies (or wavelengths) not only in the visible range, but also frequencies (or wavelengths) in the infrared, ultraviolet, and other areas of the overall electromagnetic spectrum. Also, a given spectrum may have a relatively narrow bandwidth (e.g., a FWHM having essentially few frequency or wavelength components) or a relatively wide bandwidth (several frequency or wavelength components having various relative strengths). It should also be appreciated that a given spectrum may be the result of a mixing of two or more other spectra (e.g., mixing radiation respectively emitted from multiple light sources).

For purposes of this disclosure, the term "color" is used interchangeably with the term "spectrum." However, the term "color" generally is used to refer primarily to a property of radiation that is perceivable by an observer (although this usage is not intended to limit the scope of this term). Accordingly, the terms "different colors" implicitly refer to multiple spectra having different wavelength components and/or bandwidths. It also should be appreciated that the term "color" may be used in connection with both white and non-white light.

The term "controller" is used herein generally to describe various apparatus relating to the operation of one or more light sources. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present embodiments and disclosures outlined herein. The terms "program" or "computer program" are used in a generic sense to refer to any type of computer code (e.g., software or microcode) that can be employed to program one or more processors or controllers.

Figure 2:
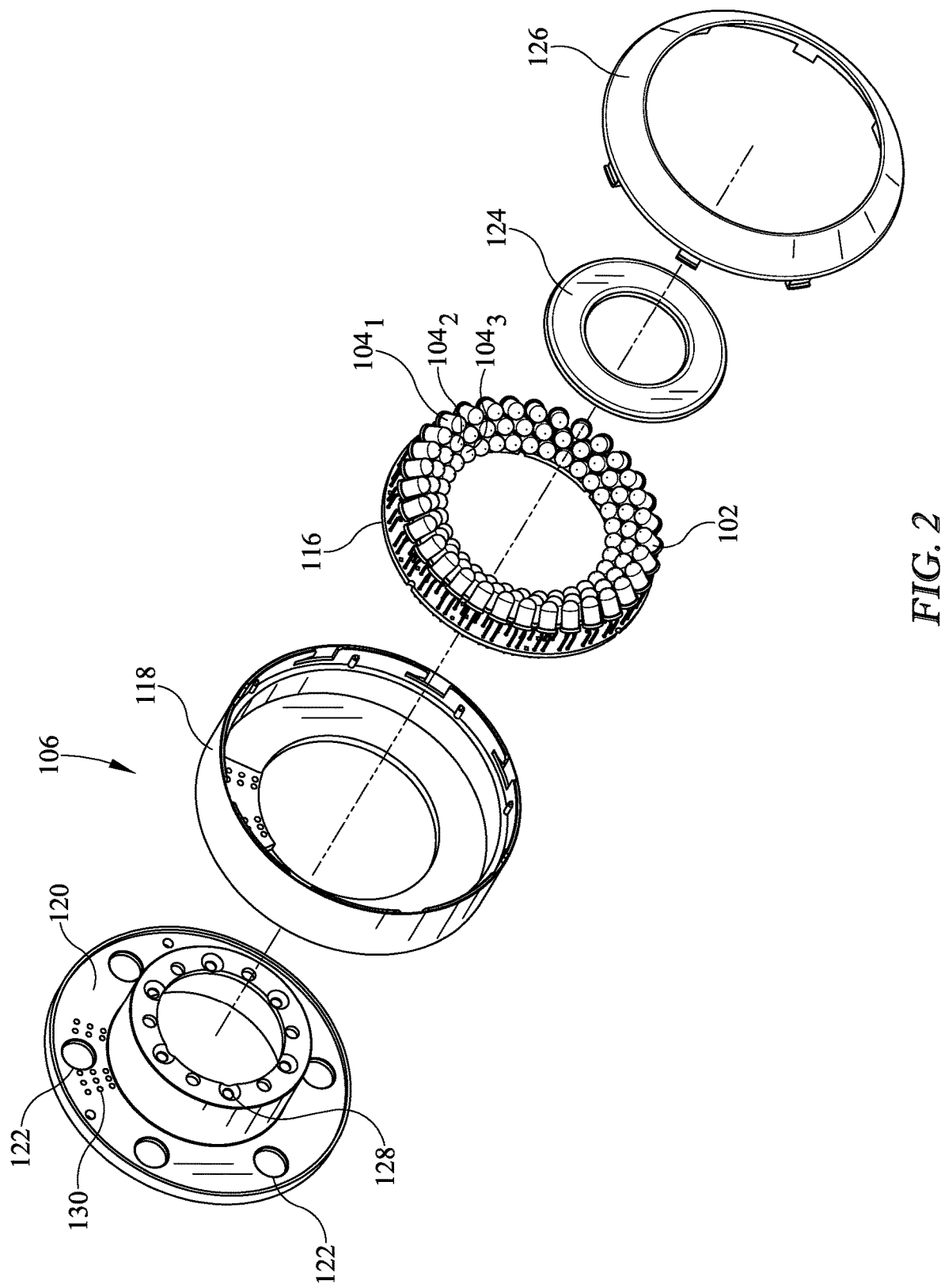
FIG. 2 is an exploded view of the modular light ring of FIG. 1 consistent with an embodiment described herein.
Figure 3:
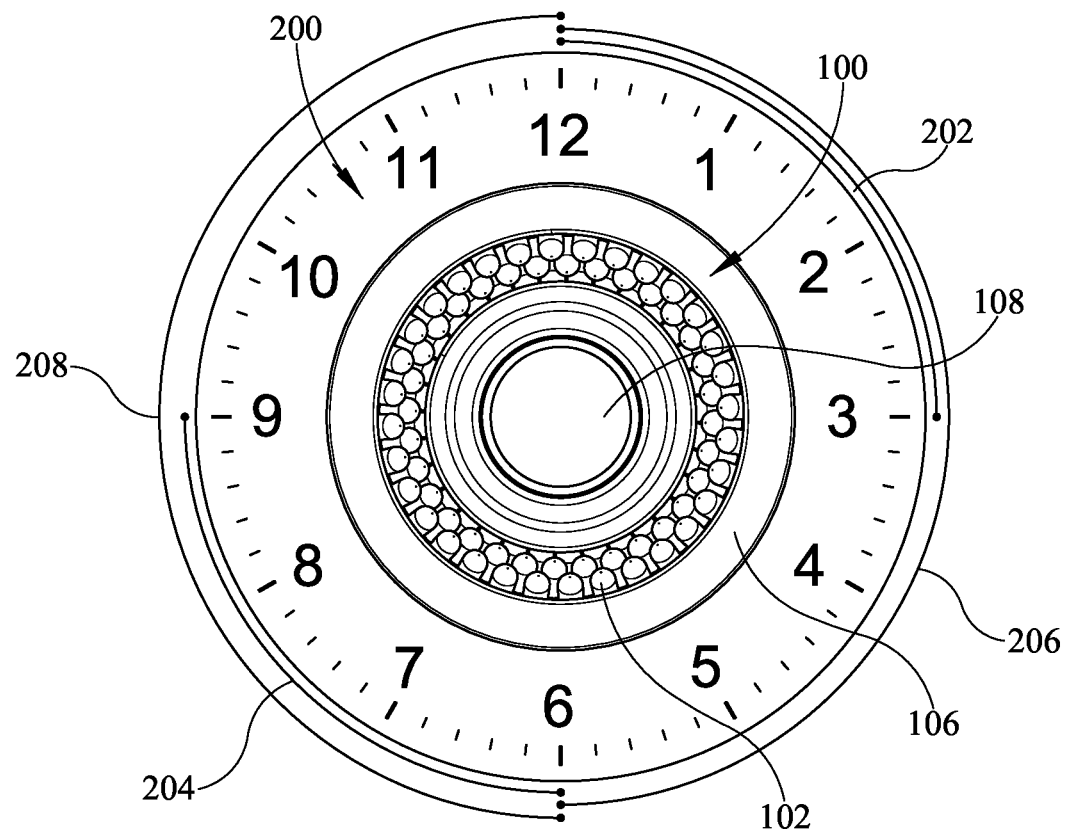
FIG. 3 is a bottom view of the modular light ring of FIG. 1 that illustrates an exemplary control map for the light ring an embodiment described herein.

Referring now to FIGS. 1-3, a modular LED based light ring 100 consistent with one embodiment disclosed herein is depicted. The light ring 100 may include a plurality of light emitting diodes (LED) 102, that may produce wavelengths within the range of about 270 nm (deep UV) to about 1000 nm (infrared). The modular light ring 100, as depicted in the various examples, may be affixed to an end effector of a bio-printer 1200, for example shown in FIG. 12, the exemplary end effector 1205

By light output characteristic, it is meant that a controller may drive the plurality of LEDs at specified light output characteristics. For example, the controller may determine an intensity or lumen level output of the LEDs within a row, section, quadrant or otherwise, by addressing the various LEDs within a group or alternatively separately by group and/or individually. The controller may define a first portion of the LEDs as a first group or similar grouping, a second portion of the LEDs as a second group or similar grouping, and so on. Each group may be defined as being of different sizes and in various locations. For example, LEDs do not necessarily need to be adjacent to be in the same group, portion or section. Each LED may therefore be addressed and controlled individually by the controller and the light output characteristic modified or determined. The controller may further drive the LEDs using known techniques, such as modulation. This modulation can be pulse based, such pulse width modulation, frequency modulation, amplitude modulation or other techniques. The controller may also identify certain of the LEDs in the plurality of LEDs, as primarily emitting a defined color or wavelength and then appropriately address those LEDs alone or in combination with other LEDs that have other colors or wavelengths to produce a known combination color or wavelength. The controller may further define groups of LEDs which constitute a portion of the LEDs mounted in the modular light ring 100 to define individual groups, defining multiple groups and or combining different locations of the LEDs together in the same group or in alternative groupings.

By individually controlling the LEDs to known output light characteristics as may be matched to a material being used and ejected from the end effector in the printing process, the controller may efficiently combine specific materials being used in the printer with known beneficial light output necessary for crosslinking or curing requirements. Such matching may be user defined and entered through the user interface or be automatic and provided to the light ring via any of a number of communication techniques directly from the bioprinter. For example, two-way communication may be provided from the bio-printer to the modular light ring 100 to cure a particular printing location or quadrant for a pre-defined duration at a pre-defined light output characteristic based upon the bio-ink utilized and the shapes and/or location of the printing process. Such information may be transmitted from the bio-printer to the modular light ring with sufficient information for illumination paired with the bio-ink. The communication may be via wired or wireless communication, through the power link between the modular light ring and the end effector, via wireless communication such as bluetooth or other similar means, utilizing near field communication techniques, or other communication protocols. Handshaking between the light ring and the bio-printer may also occur verifying receipt of the data, as well as control information on specific required lighting characteristics needed for crosslinking/curing, when to initiate the curing process, time requirements for curing, location information as to where the bio-printer is printing, and similar process related curing data.

For example, a bio-printer (see 1200 in FIG. 12) may be used to print different materials in differing sectors of a substrate. Each of these different materials may have varying curing or crosslinking requirements. In some implementations, the light output characteristic of the light ring 100 may be modified to a required light characteristic, by sector. The curing or crosslinking may be affected by a process which is initiated by control of the light output characteristic, by sector, of the modular light ring 100. In these implementations, fine control of the curing or crosslinking process can be maintained. As a non-limiting example, a cell-laden gelatin methacryloyl hydrogel that includes a photoinitiator (e.g. Irgacure 2959) may be printed into a petri dish or other suitable sterile container. These may then be cured or crosslinking at a wavelength of 365 nm and an irradiance of 1000 mW/cm$^2$ for an exposure time of approximately 10 seconds, in order to achieve the desired crosslinking. This is not to be understood as limiting, as it would be understood that these wavelength, irradiance, and exposure time may vary based on the specific cell component, the carrier (e.g. hydrogel ink), and/or the specific photoinitiator used.

Additional control may include communication between the bio-printer (see 1200 in FIG. 12) and the light ring as to when the curing process needs to begin, location of the printed material, time duration of the curing process, intensity of illumination and lighting characteristics needed to accomplish the curing process, etc. Further the bio-printer may control such process in limited fashion or not at all, by merely providing a signal of when to initiate curing while leaving the specifics as to duration, location or any other curing process requirements to be selected and controlled by a user or determined by the light ring itself.

In one embodiment illustrated in FIGS. 1-3, LEDs 102 are utilized and arranged in three circular rows $104_{1-3}$ or concentric or annular ring arrays which may or may not be physically mounted on or near a printed circuit board (PCB) 116. The design illustrated in FIGS. 1-3 accommodates the placement of multiple LEDs in a desired pattern, allowing for a plurality of illumination wavelengths (e.g. ultraviolet, visible, infrared, etc.) from a single lighting apparatus or source. The plurality of rows can be positioned in an annular relationship within the modular light ring housing 118. The rows 104 may further be positioned in a manner such that each row is at a different elevation relative to the other rows in order to encase a higher number of LEDs within a small footprint or to better control the light output characteristics. In some examples, the rows 104 may be arranged so that particular color LEDs are in predefined rows or are spaced intermittently within rows. Such positioning of the rows along different elevational positions may also aid in color/wavelength mixing or intensity adjustment. In further instances, the layout of the modular light need not be a circular arrangement or an array; there may be instances where a square, rectangular, elliptical arrangement may be beneficial in order to better accommodate and integrate to a particular tool or end effector design.

By elevational position it is meant that the LEDs in the rows may be located at different distances from a light emitting/output plane of the light ring. For example, row $104_3$ may be further from the light emitting/output plane at the open end of the light ring than row $104_2$, which itself may be further from the light plane than row $104_1$. Further mounting characteristics of the LEDs may include rotating the central mounting axis at different angles relative to the light output plane. For example, row $104_3$ may be mounted at a higher angle relative to the light output plane than row $104_2$, and row $104_2$ may have LEDs which are mounted at higher angle relative to row $104_1$ all relative to the light output plane. Other alternative mounting axis tilts may also be implemented to vary the light output axis of rows, quadrants, segments or groups of LEDs. In other embodiments as depicted in the figures, the central mounting axis of the LEDs in the various rows may be equal relative to other rows. Further, the light output plane may be defined as a plane across opening 108. Differences in elevation positions (or a stadium seating like arrangement), such as illustrated in the exemplary embodiments, may allow for a greater density of LEDs. A greater density of LEDs may provide a greater lumen output, which may be beneficial for particular bioinks requiring a higher lumen output for crosslinking.

It is to be understood that such the concentric circle arrangement of the LEDs illustrated in FIGS. 1-3 is not to be construed as limiting, as in some instances there may be only two rows LEDs, while in other instances there may be four or more rows of LEDs. Further, in some implementations, different LEDs may be located within the circular rows, each individual LEDs capable and/or specialized to generate light in defined wavelengths. For example, specialized LEDs may be placed within individual circular rows or in coordinated positions to more efficiently emit light of desired wavelengths. When light emissions within defined wavelengths are required, a controller (see 1305 in FIG. 13) can utilize the subset of LEDs that more efficiently emit light at the desired wavelengths to increase efficiency of the light output.

The LEDs depicted may be electrically connected to a power source integrated within the end effector or may be independently powered. The power supply may be AC or DC power or may be power configured specifically for driving the LEDs in segments or groups, or individually. For example, the power supply may be a DC power supply that is sufficient to power and control each of the LEDs in the plurality of rows depicted. Such power supply can be integrated within a controller such that the plurality of LEDs are driven at the necessary frequency to generate a desired output in wavelength, intensity, frequency and the like. Alternatively, the power supply (see 1310 in FIG. 13 may be separated from the controller so as to provide ample power to the loads depending on the user settings, the controller then modifying the drive signals to the individual or grouped LEDs. For example, a standard DC power supply may be integrated into the end effector and provide typical but not limited to 12V or 24V as needed. The controller 1305 can be configured to drive the LEDs based upon the available power to produce the necessary light output.

In some implementations, the controller 1305 may implement frequency modulation to drive the LEDs. In other embodiments, amplitude modulation can be utilized. In the various embodiments, control of the light output for the plurality of LEDs may be implemented by a single controller, multiple controller or controllers and/or combined drivers for each LED. LED controllers can be positioned on the board to which the LEDs are mounted or may be separately integrated in other hardware. Further, LED drivers may be integrated, where needed, separate from the controller or combined therewith. For example, an LED controller may be implemented that both powers the LEDs at necessary times, as indicated by a user interface, and which controls a separate LED driver to drive the LEDs accordingly to desired illumination output characteristics. Such drivers can be positioned on the dye or be separated therefrom as well. In other implementation, single form electronics may be utilized to both control and drive the LEDs.

In implementations, the PCB and LEDs 102 contained thereon may be controlled by sector and row. Under such control, a particular row or sector may be activated at a particular intensity/irradiance value, allowing a user higher exposure and dosing control during use. This fine level of control may be especially valuable during bio-printing and curing or crosslinking of biological or engineered materials. A non-limiting example of defining multiple sectors or rows is illustrated in FIG. 3. FIG. 3 is a bottom view of the light ring 100 with a clock-like scale 200 circumscribing the light ring 100. This clock-like scale 200 forms no part of the light ring 100, and is solely presented herein to facilitate description of the light ring 100. As mentioned previously the LEDs 102 of the light ring 100 may be divided into a plurality of sectors. FIG. 3 provides a non-limiting example of these plurality of sectors. For example, in some implementations, the user could utilize the clock-like scale 200 depicted in FIG. 3. A sector on the clock face of the user interface is selected which may also trigger opening of a dialog box on an associated display device. The irradiance value of the LEDs may be entered through the dialog box for the selected sector of LEDs.

In one illustrative example, each row $104_{1-3}$ or concentric ring array of LEDs 102 is divided into sectors of varying sizes. As illustrated, a first row $104_1$ (the row nearest the opening 108) has four sectors dividing the LEDs 102 of the first row $104_1$ of the light ring 100 into sectors/quadrants (e.g. 12-3, 3-6, 6-9, and 9-12 on the clock-like scale). In FIG. 3, two of these sectors are marked by lines 202, 204. As illustrated, a second row $104_2$ (the middle row) and a third row $104_3$ each have two sectors dividing the LEDs 102 of the second row $104_2$ and the third row $104_3$ of the light ring 100 into halves (e.g. 12-6 and 6-12 on the clock-like scale). In FIG. 3, one of the two sectors of the second row is marked by line 206; while one of the two sectors of the third row is marked by line 208. These illustrated sector examples are not intended to be limiting as, for example, still using the clock-like scale 200 of FIG. 2, the LEDs 102 of the light ring 100 may be divided into three sectors (e.g. 12-4, 4-8, and 8-12). It is to be understood that the LEDs 102 of particular row 104 of the light ring 100 may be divided into any number of sectors as deemed necessary. Each sector, may be separately activated at a particular intensity/irradiance valve. In some instances, only a particular sector(s) may be illuminated, while in other instances, all of the sectors may be illuminated simultaneously. In implementations, LEDs will be activated in a full circular pattern to provide even illumination towards a target area. Desirable illumination characteristics may be selected through the user interface for a particular print or curing application. In these implementations, while a full circular illumination pattern will be emitted from the LEDs 102, the user interface will allow setting of desired light output characteristics for selected sectors of LEDs so that subsets of the LEDs are identified for desired light output modification.

In still further examples, each row of LEDs $104_{1-3}$ may utilize different types of LEDs. For example and as described further herein, a row or sector/quadrant of primarily red wavelength LEDs at around 620-750 nanometers, may be provided. Another row of primarily blue wavelength light LEDs may be provided at about 450 nm-495 nm. Similar variations may be provided at different quadrants/sectors and along different rows. By mixing different light output characteristics, both frequency mixing and specific frequency output may be implemented, by quadrant, utilizing the modular light ring depicted in at least one of the examples provided. Driving each of the LEDs for proper light output characteristic may also be implemented separately or jointly using various LED drivers and controllers, as described herein.

In some embodiments, the LEDs of the light ring 100 may have multiple wavelengths available for use based on, for example the materials being printed and/or workflow needs. Examples of such wavelengths may include, but are not limited to: ultraviolet light spectrum, which may be about 365 nm to about 400 nm; visible light spectrum, which may be about 400 nm to about 700 nm; and infrared light spectrum, which may be about 700 nm to about 1000 nm. In some instances, it may not be necessary for all of the LEDs 102 of the light ring 100 to be simultaneously illuminated. Instead, the light trajectories and/or vectors from the individual LEDs 102 may allow the user greater control over crosslinking or curing, depending on the material and/or workflow need. For example, the LEDs may be controlled by sectors around the annular light ring (sector control), by circular row 104 (row control), or by a combination of the two (as illustrated in FIG. 3).

In some embodiments, the controller may allow the user to define individual rows and individual sectors/groups to be illuminated. Sectors or groups may be individual LEDs collectively grouped together, whether or not they are adjacent or in the same row. Further, the controller may allow for the LEDs in the plurality of sectors and rows to be controlled for particularized output. For example, an application may require the left side output of sector 12-6 to be at a desired wavelength and at a desired lumen output, or in lux. Lux may take into account the area of luminous flux whereas the lumen output does not. In such implementation, LEDs in sector 6-3 may be required to be driven at a second different wavelength and/or intensity while LEDs in sector 3-12 may be required to be driven at a third different wavelength and/or intensity. The controller allows the user to define the different sectors and the different light output characteristics for each of the individual sectors.

Referring specifically to FIG. 2, an exploded view of the light ring 100 is illustrated. The light ring 100 may include a housing 106, which may be constructed of any suitable, durable material known in the art. In some instances, such as illustrated in FIGS. 1-3, this housing 106 may roughly cylindrical in shape similar to the arrangement of the LEDs 102. However, this is not to be understood as limiting as the shape of the light ring 100 may vary; although the shape of the housing may generally follow the arrangement of the LEDs 102. Additionally, in some instances, the housing 106 may further include a main housing body 118 and a back cover 120. The back cover 120 of the housing 106 may, in some instances, additionally include one or more magnets 122, or may be at least partially constructed of a magnetized material, to allow for removable attachment to an end effector, as described in detail with reference to FIGS. 4-9. The back cover 120 may further include one or more electrical connection portions 130, such as, for example, spring pins or other electrical contacts that are described with reference to FIG. 6. In some instances, the back cover 120 may additionally include one or more mechanically couplings 128 for rigidly mounting the light ring 100 to the end effector. The housing 106 of the light ring 100 may also further include, in some instances, an inner fastener 124 and an outer fastener 126, each of may individually or in combination facilitate the attachment of the LEDs 102 to the main housing body 118.

The light ring 100 may, in some instances, have an opening 108 in the center of the light ring 100 capable of receiving an end effector and the dispensing barrel tip (see FIGS. 4-10) or a machine vision application, such as an optical sensor which is positioned into an interior of the ring and directed towards a work area that is illuminated by the light ring 100. In such implementations, the light ring may provide desired illumination of a work area which is scanned by an optical sensor for input into an automated vision system. For example, an automated vision system may detect certain light reflective characteristics present when a desired reaction has completed. At such time, the vision system may automate switching off the illumination ring to prevent further light activated reactions. Automated vision systems may assist in visualizing flaws and features of various parts under inspection which may not be seen by direct illumination in line with the camera source. The opening 108 may also define a light output plane of the light emitted by the LEDs, the plane extending across the opening.

Referring now to FIGS. 4-7, a light ring 300 mounted on an end effector 305 is generally depicted. In the illustrated embodiment, the light ring 300 is similar to that of FIGS. 1-3, including bulb-style LEDs 302 are utilized and arrange in three circular rows $304_{1-3}$ or concentric ring arrays on a printed circuit board (PCB) 306. The PCB may contain all necessary circuitry for driving and controlling the plurality of LEDs 302. For example, the PCB may have at least one microcontroller or microprocessor, power supply and/or power supply couplings, memory, driver electronics and/or any other electronics necessary for powering and illuminating the LEDs. As well, the memory may contain instructions which are executed by the at least one microcontroller or microprocessor for controlling the plurality of LEDs. These instructions which are executed by the at least one microprocessor or controller may include instructions for controlling the LEDs at particular frequencies, intensity levels, color mixing or other light output characteristics, and also for storing user instructions received from a user interface for specific predetermined illumination characteristics. Such illumination characteristic may include sectors, rows, colors, intensity or additional lighting characteristics necessary for curing and/or crosslinking the material emitted from the bio-printer. Such instructions may also include appropriate information for illuminating all or only a portion of the printed substrate for such curing, and for a time period which is either a default or a user-defined time period based upon the materials being used. Separate controllers or microprocessors may be utilized for different functions. For example, a separate controller may be tasked with communication, control of external electronics, communication with individual drivers for the LEDs, or combined into a programmable microcontroller having outputs to control addressing, drivers, communication chips and the like.

The end effector 305 may be, for example, an end effector of a 3-D printer (see FIG. 12) such as, for example a BioAssemblyBot®, as produced by Advanced Solutions Life Sciences, located in Louisville, Ky. More specifically, the end effector 305 illustrated in FIGS. 4-7 is coupled at a distal end of the robotic arm of a bioprinting system, which may include one or more dispensing tips 315 and syringes (e.g. a 30 cc hot syringe 320) each including a 3D printable material, which may be either a non-bio material or a bio-material. However, it is noted that the light ring 300 described and illustrated herein may be used with any robotic assembly utilizing robot end effectors or other application where precision lighting solutions may be beneficial (e.g. machine vision applications, robotic microscopes, robotic pick and place systems, robotic surgery systems, and the like.)

In the illustrated embodiment, the dispensing tip 315 may be configured to dispense the 3D printable material. Once dispensed, or simultaneous with the bioink being dispensed, the light ring 300 may be utilized to facilitate crosslinking and/or curing of the dispensed material. For example, if a liquid "bioink" containing cells were dispensed, the crosslinking may allow for formation of a chemical bond between two polymers, protein chains, or two different parts of the same chain to cure or "set" the printed material. At a non-limiting example, the bioink may include gelatin/alginate blends for printing cells in a 3D environment. Concentrations from approximately 4% to 10% gelatin and 3% to 9% alginate. These materials may be dissolved in phosphate buffered saline (PBS) and sterile filtered prior to combining with desired cell types (e.g. mesenchymal stem cells, induced pluripotent steam cells, chondrocytes, etc.). As a non-limiting example, gelatin methacryloyl (GelMA) may be used with a photoinitiator such as Irgacure 2959.

The intensity and/or irradiance needed to cure or "set" the printed material may vary depending on the material itself. Therefore, in some instances, it may be desirable for the light emitting diodes to be capable of producing light within, for example, the ultra violet spectrum (e.g. about 365 nm to 400 nm), the visible spectrum (e.g. about 400 nm to about 700 nm), and the infrared spectrum (e.g. about 700 nm to about 1000 nm), or a combination thereof in different portions of the light ring 300 such as illustrated with reference to FIGS. 1-3.

Figure 4:
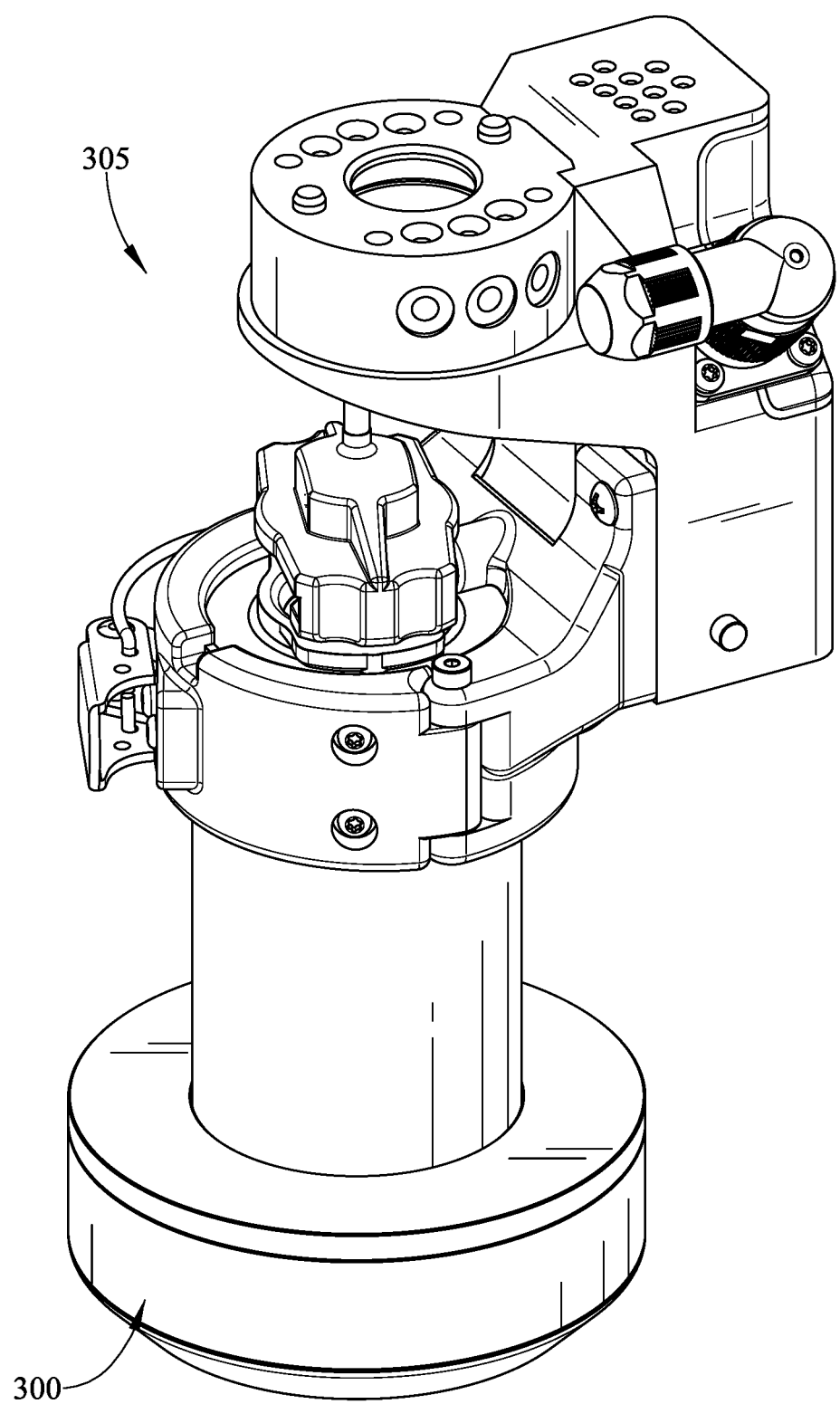
FIG. 4 is perspective view of a modular light ring consistent with an embodiment mounted to an end effector consistent with an embodiment described herein.
Figure 5:
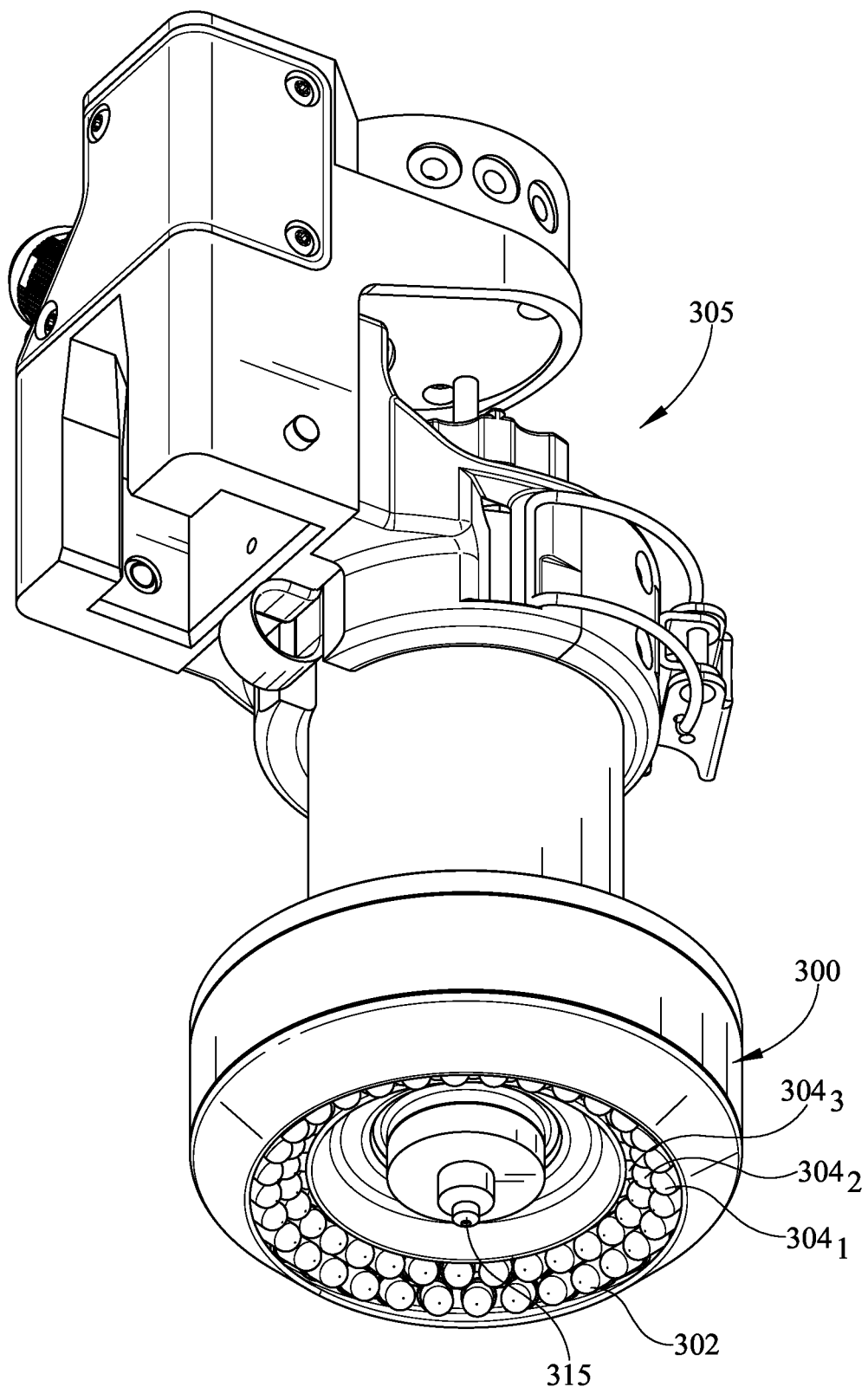
FIG. 5 is a lower perspective view of the modular light ring and end effector of FIG. 4 consistent with an embodiment described herein.
Figure 6:
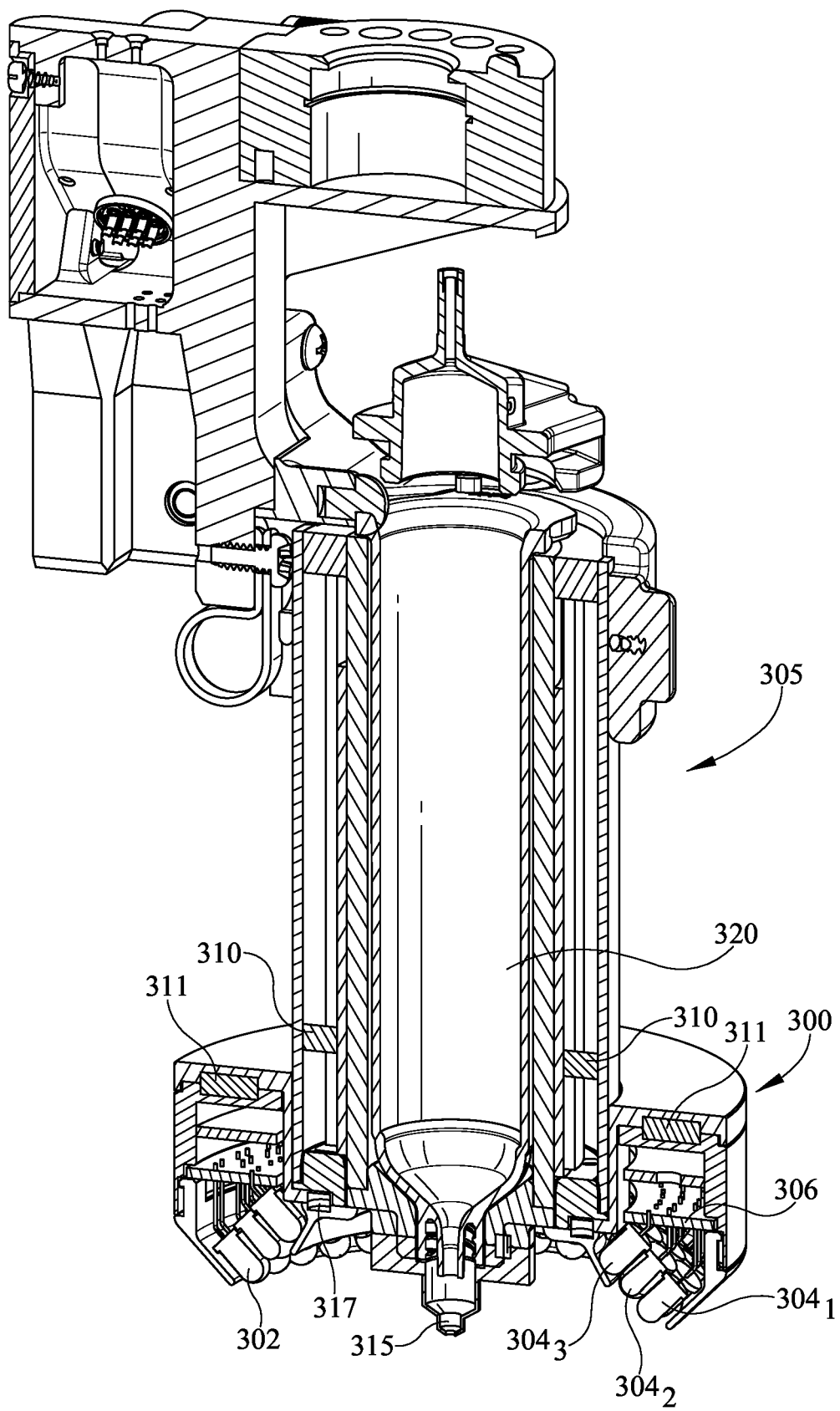
FIG. 6 is a cross-sectional view of the modular light ring and end effector of FIG. 4 consistent with an embodiment described herein.
Figure 7:
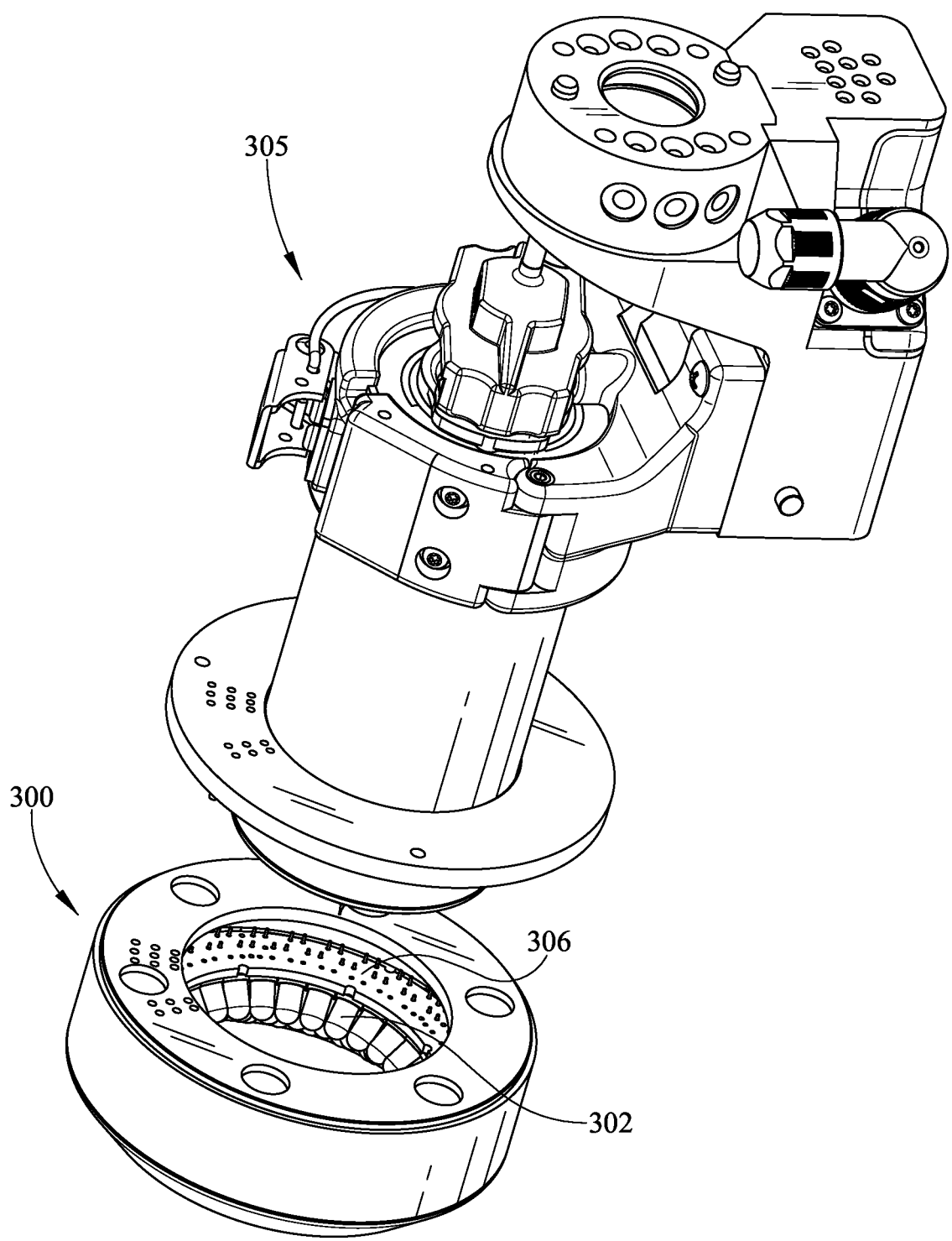
FIG. 7 is a perspective view of the modular light ring and end effector of FIG. 4 with the ring light removed from the end effector consistent with an embodiment described herein.

The light ring 300 may be configured to removably couple with an end effector, such as end effector 305, in order to provide light exposure for curing/crosslinking. For example, FIGS. 4-6 illustrate the light ring 300 coupled with the end effector 305, whereas FIG. 7 illustrates the light ring 300 removed from the end effector 305. In some instances, the light ring 300, is coupled to the end effector 305 through the use of one or more couplings such as interfacing magnets 310, 311. In implementations, one or more magnets 311 may be disposed within the light ring 300 and/or the end effector 305 to allow the light ring 300 to be removably positioned on the end effector. Magnets may be located in various locations allowing the end effector to locate the light ring near the dispensing end of the end effector and direct light towards the bioink dispensing work area. In other such instances, the light ring 300 and/or the end effector 305 may be constructed of a magnetized material. However, this is not limiting, as in other instances the light ring 300 may be coupled to the end effector 305 through a screw-type interface where the light ring 300 may be threaded onto the end effector 305. In still other instances, the light ring 300 may be coupled to the end effector 305 using a snap-fit assembly method where each of the light ring 300 and the end effector 305 contain interlocking parts that may be pushed together in order to couple them to one another. Additionally, any other method of removably mechanically coupling known in the art may also be used. Furthermore, the light ring 300 may be both coupled and removed by a user's hands, or may be automatically coupled and removed through the use of robotics or other removal mechanisms.

Further aspects of the light ring may include an electrical coupling 317 between the light ring 300 and electrical power supplied by the end effector 305. In some of these instances, electrical connections utilized on the light ring 300 interface with the end effector 305. In one implementation, spring pins or other electrical contacts 317 align and electrically connect the end effector with the light ring at the interface between the two structures. As a non-limiting example, these spring pins may removably couple to an electrical contact pad of the end effector 305 so that electrical power and communication signals may be sent from the end effector 305 to the light ring 300 as well as LEDs 302 to produce light. In implementations, the electrical connection may also allow for a communication interface between the light ring 300 control electronics and a computer external interface for entry of the various light output characteristics. In other embodiments, the light ring 300 may have an independent power source, such as a battery or other plug-in power source which plugs directly into an electrical interface on the light ring, which itself may communication wirelessly or through the electrical connection to a related computer or other control interface. In still other embodiments, the light ring 300 may use a combination of power sources.

The electrical coupling or interface 317 between the light ring 300 and the end effector 305 may also act as a communication pathway between the electronics of the light ring 300 and control electronics of the bio-printer. For example, the bio-printer may transmit specific information to the light ring related to the needed light output characteristics necessary for curing the associated bio-ink. Additional other curing related data may be transmitted by a transmitter in the bio-printer or in the end effector to a light ring communications receiver which receives the curing data and implements the necessary curing data specifics for the related bio-ink.

Figure 8:
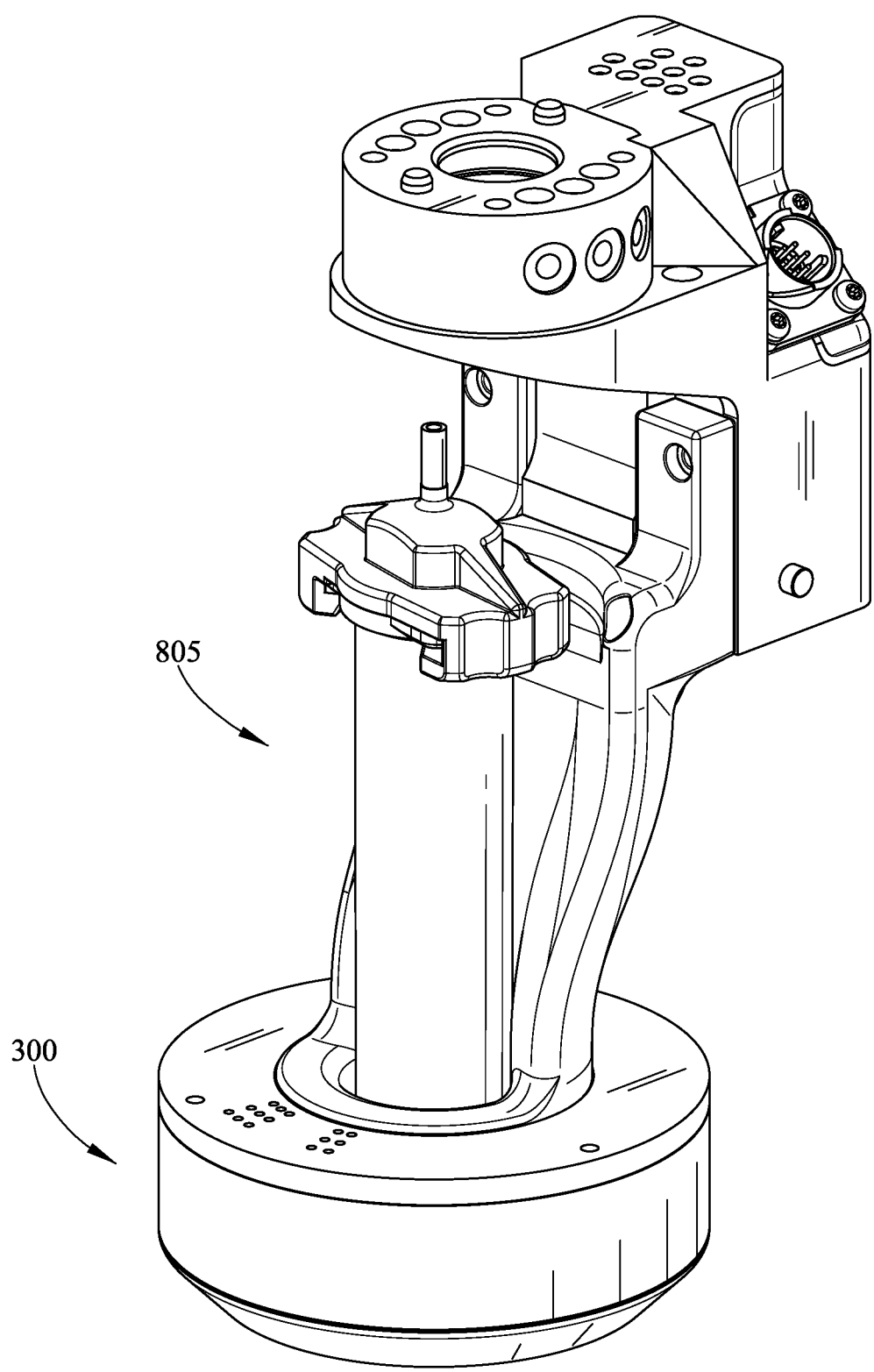
FIG. 8 is perspective view of a modular light ring consistent with an embodiment mounted to another end effector consistent with an embodiment described herein.
Figure 9:
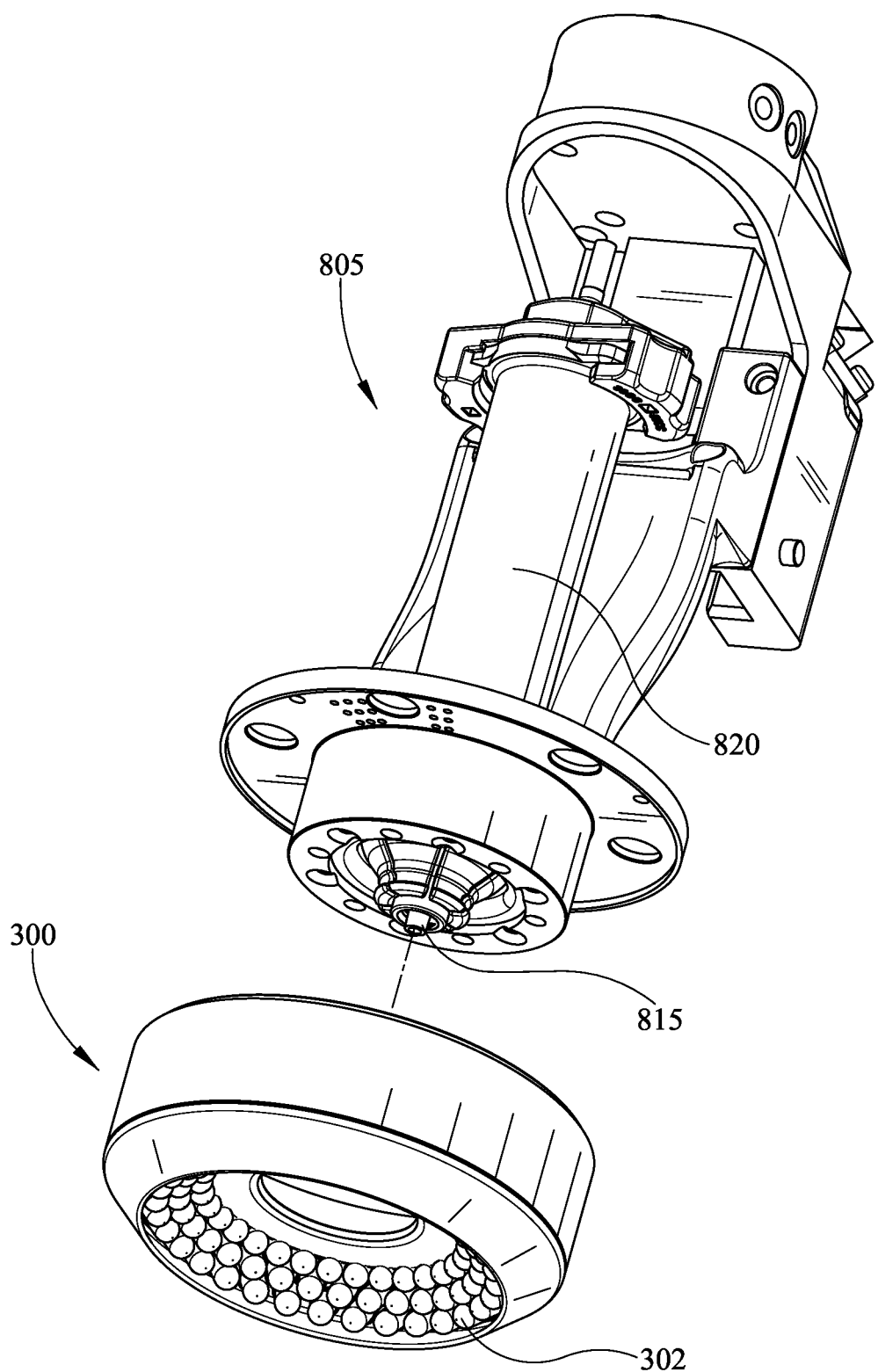
FIG. 9 is a lower perspective view of the modular light ring and end effector of FIG. 8 consistent with an embodiment described herein.
Figure 10:
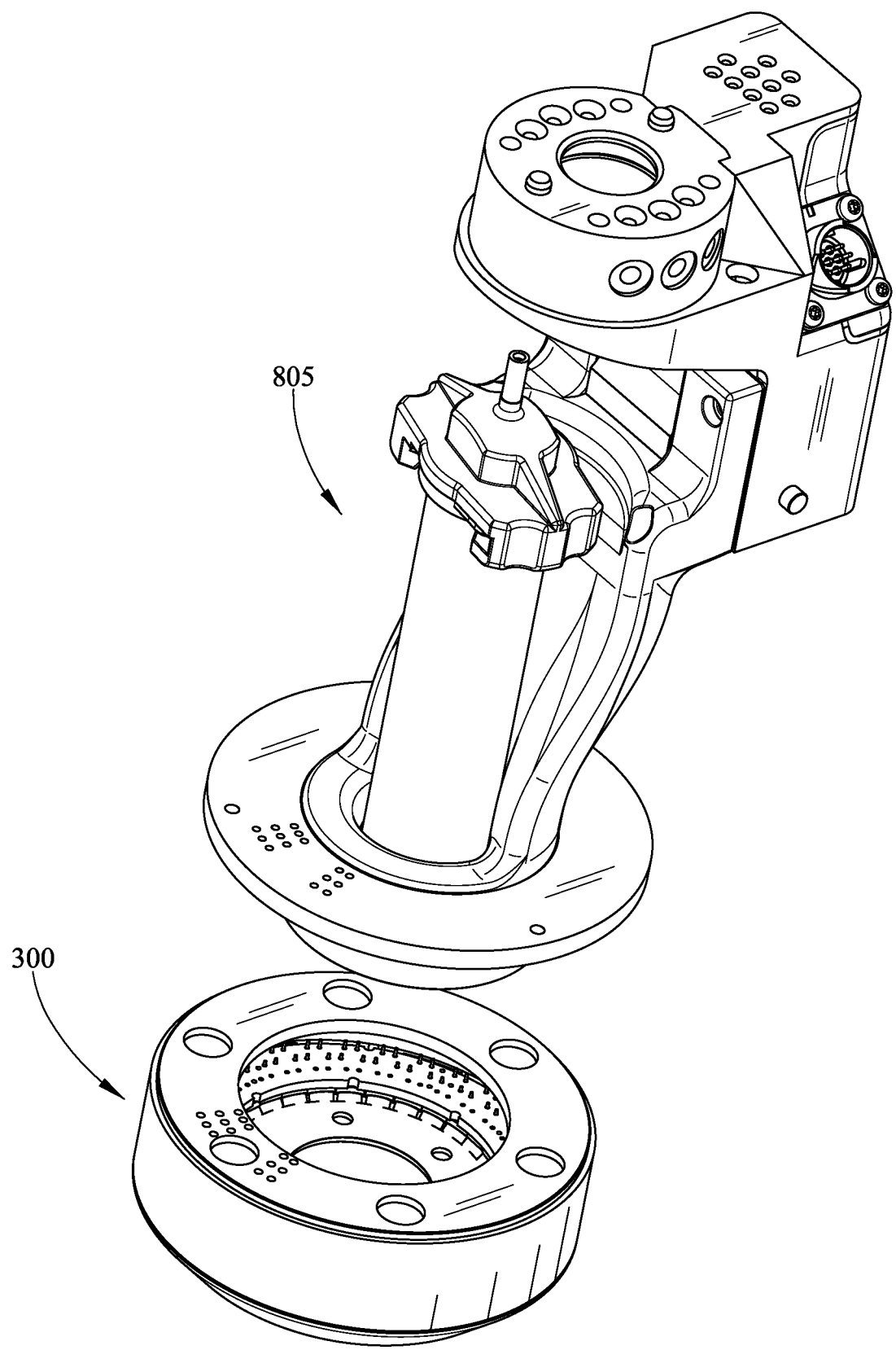
FIG. 10 is a perspective view of the modular light ring and end effector of FIG. 8 with the ring light removed from the end effector consistent with an embodiment described herein.

Referring now to FIGS. 8-10, the light ring 300 described with reference to and illustrated in FIGS. 4-7 is now illustrated mounted on another end effector 805. This end effector 805 may be, for example, an end effector of a 3-D printer (not illustrated). More specifically, the end effector 805 illustrated in FIGS. 8-10 is coupled at a distal end of the robotic arm of a bioprinting system, which may include one or more dispensing tips 815 and syringes (e.g. an ambient syringe 820) each including a 3D printable material, which may be either a non-bio material or a bio-material. FIGS. 8-9 illustrate the light ring 300 coupled with the end effector 805, whereas FIG. 10 illustrates the light ring 300 removed from the end effector 805.

Figure 13:
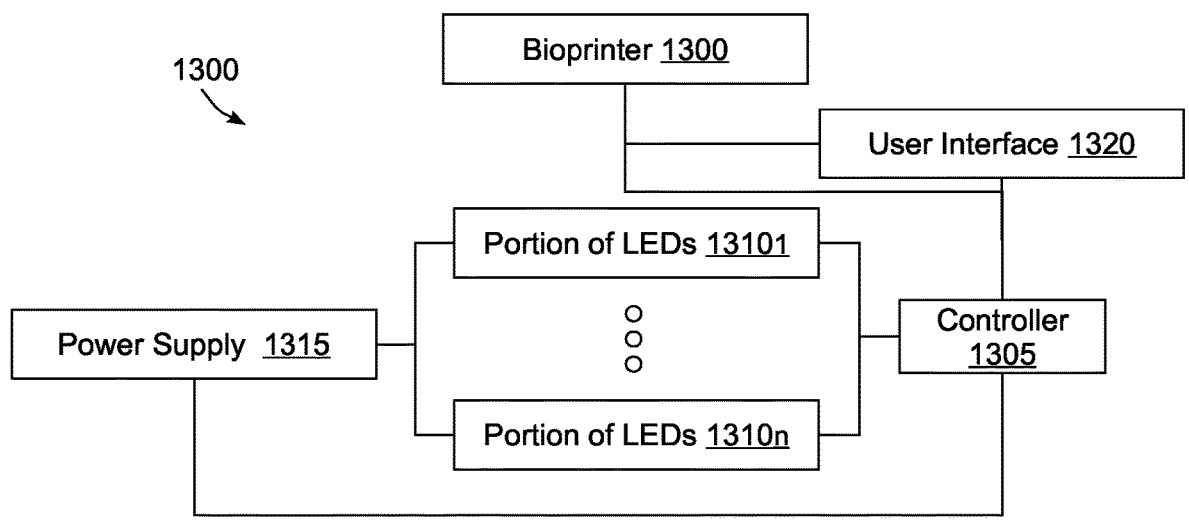
FIG. 13 is an exemplary block diagram showing various elements of the control system 1300 for the modular light ring.

Referring now to FIG. 13, a block diagram showing various elements of the control system 1300 for the modular light ring are illustrated. As described in detail throughout, FIG. 13 illustrates that the controller 1305 may receive one or more light output characteristics either directly from the bio-printer 1300 or from the user interface 1320. These light output characteristics may correspond to the first, second, etc. portions of the LEDs $1310_{1-n}$. These portions of the LEDs $1310_{1-n}$ may be annular rows, sectors, or the like. The controller 1305 is further connected to the portions of the LEDs $1310_{1-n}$ and the power supply 1315 to provide information regarding the light output characteristics to both. The controller 1305 may drive the light output characteristics using the power 1315. As described previously, the controller 1305 may drive a second portion of LEDs to achieve a different light output characteristic from the first set of LEDs.

Figure 11:
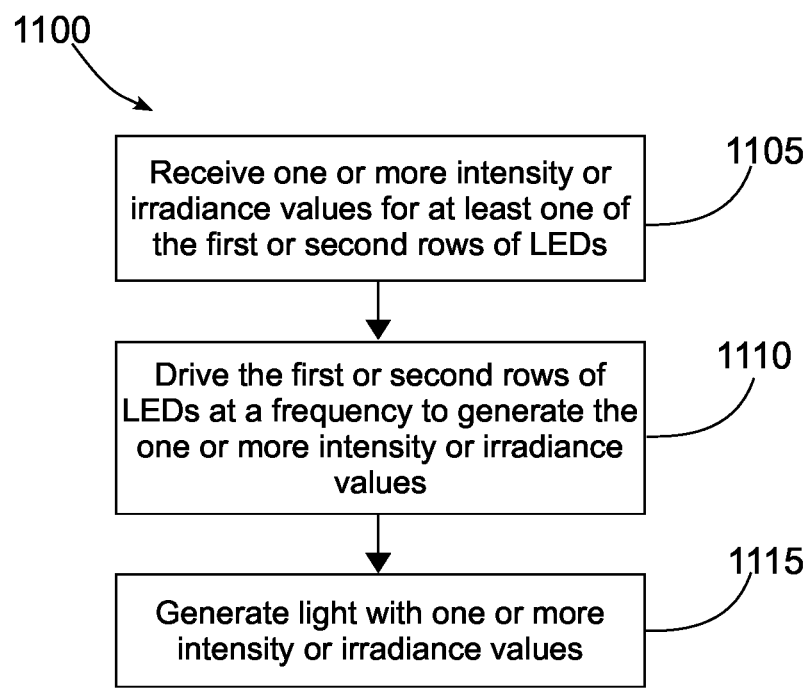
FIG. 11 is a flowchart illustrating an example method of configuring a modular light ring.

Referring now to FIG. 11, a flowchart illustrating an example method 1100 of configuring a modular light ring, such as the modular light ring 100, 300 illustrated in and described with reference to FIGS. 1-3 or FIGS. 4-10, is provided. The modular light ring may, at block 1105, receive one or more intensity and/or irradiance values for a first and/or second row of LEDs. These intensity or irradiance values may be entered by a user into a user interface. In some instances, the user interface may be in the form of a dialog box on an associated device where a user may enter one or more values (e.g. intensity and/or irradiance) for each row of LEDs. For example, a dialog box may be provided in a remote device, such as a phone or other computing device, in communication with the modular light ring. Alternatively, the user interface dialog box may be implemented through the control system of the bio-printer. In other instances, the user interface may be a clock-like scale circumscribing the light ring (see FIG. 3) for entering one or more values (e.g. intensity and/or irradiance) for each row of LEDs. In some instances, a user may desire all LEDs of all rows of the light ring may be illuminated to provide certain light output characteristics (as determined by the entered intensity and/or irradiance); while in other instances, a user may selectively illuminate only a single row of LEDs.

Data received from the user interface may include curing data which includes specifics for both curing of the bio-ink and crosslinking information. Such curing data may include region, sector, quadrant, grouping information for the specific LEDs that are necessary to be illuminated. Other curing data may include light output characteristics by each of said region, sector, quadrant or grouping of the LEDs.

Once the one or more intensity and/or irradiance are received for the rows of LEDs, the selected LEDs may be, at block 1110, driven by a power supply at the frequency necessary to achieve the intensity and/or irradiance values received. As described previously, the power supply may be independently powered within the light ring, may be integrated within a controller such that the plurality of LEDs are driven at the necessary frequency to generate a desired output in wavelength, intensity, frequency and the like, or may be separated from the controller so as to provide ample power to the loads depending on the user settings. Using the power supply, the LEDs in the desired rows generate, at block 1115, light with the user indicated intensity or irradiance values.

Furthermore, in some instances, the rows of LEDs may each be further divided into one or more sectors. For example, as illustrated in FIG. 3, the LEDs of each row may be further divided into quadrants (e.g. 12-3, 3-6, 6-9, and 9-12 on the clock-like scale). These sectors may be controlled similarly to the rows. For example, where the LEDs are further divided into sectors, a user may enter into a user interface intensity and/or irradiance values for one or more of the sectors, either in place of or in addition to the rows. The power supply may similarly power each sector and/or row individually at a frequency to generate the intensity and/or irradiance values entered by the user. Finally, the LEDs in the desired sectors and/or rows may generate light at the user indicated intensity or irradiance values.

Figure 12:
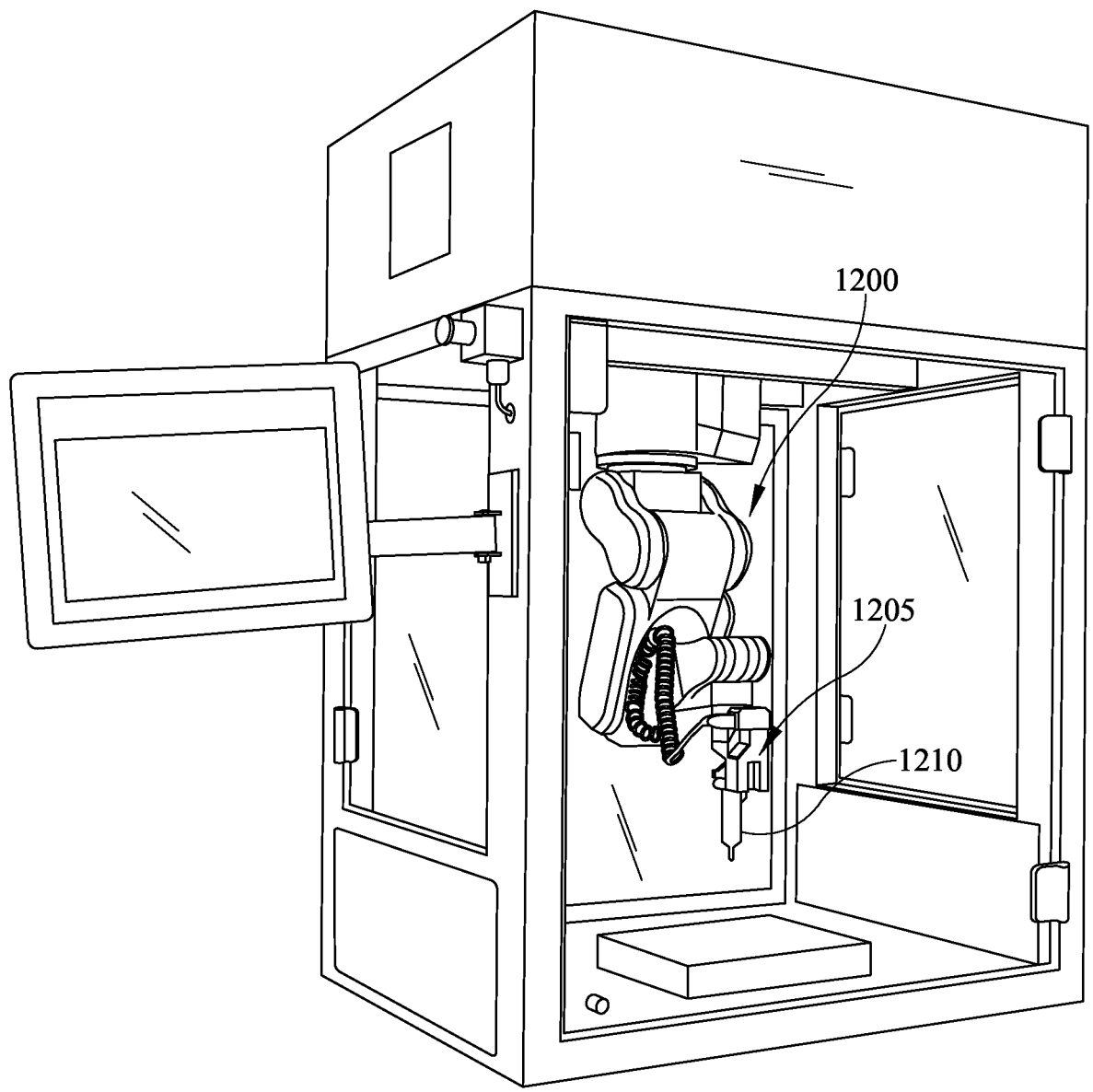
FIG. 12 is a perspective view of a bioprinter using a robotic arm end effector having aspects of the modular light ring disclosed herein.

FIG. 12 illustrates an exemplary a bio-printing robot 1200. This bio-printing robot 1200 also includes an exemplary end effector 1205 with a syringe 1210, such as those end effectors illustrated and discussed with reference to FIGS. 4-10. Although not illustrated in FIG. 12, the end effector of FIG. 12 would also be capable of receiving the modular light ring described through, for example as described with reference to FIGS. 1-3.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

When used in this specification and the claims as an adverb rather than a preposition, "about" means "approximately" and comprises the stated value and every value within 10% of that value; in other words, "about 100%" includes 90% and 110% and every value in between.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A modular light configured to removably attach to a bio-printing robot end effector, comprising:
    an annular modular light ring housing with an annular opening configured to receive the end effector of a bio-printing robot;
    the annular modular light ring housing substantially surrounding a dispensing tip of the bio-printing robot end effector;
    a power supply interface to receive electrical power from the bio-printing robot end effector
    the annular modular light ring housing removably replaceable around the dispensing tip of the bio-printing robot end effector;
    a plurality of LEDs positioned annularly around the end effector within the annular modular light ring housing, wherein the plurality of LEDs are spaced in at least two annular rows, wherein each of said plurality of at least two annular rows are at a unique elevational position within the annular modular light ring housing with respect to a light output plane of the annular modular light ring housing;
    the plurality of light emitting diodes (LEDs) in electrical communication with the power supply interface; and
    at least one controller communicatively coupled with the plurality of light emitting diodes and the power supply interface, the at least one controller configured to:
        receive, from a user interface, one or more light output characteristics;
        drive the plurality of LEDs defined by LED row information and LED sector information, at a frequency to generate the one or more light output characteristics.

2. The modular light of claim 1, wherein the annular modular light ring housing is removably replaceable with at least one magnet adjacent the bio-printing robot end effector and an interfacing magnet in the annular modular light ring housing.

3. The modular light of claim 1, wherein the annular modular light ring housing is removably replaceable with at least one mechanical interface between the bio-printing robot end effector and the annular modular light ring housing.

4. The modular light of claim 1, wherein the power supply interface is an electrical contact configured to electrically connect the end effector and the modular light.

5. The modular light of claim 1, wherein the plurality of light emitting diodes are disposed on a printed circuit board.

6. The modular light of claim 1, wherein the plurality of light emitting diodes includes:
    a first portion of the plurality of light emitting diodes; and
    a second portion of the plurality of light emitting diodes;
    wherein the first and second portions of the plurality of LEDs emit light at a different light output characteristics.

7. The modular light of claim 6, wherein the first and second portions of the plurality of light emitting diodes are each divided into a plurality of sectors, wherein each of the plurality of sectors is separately controlled by the at least one controller.

8. The modular light of claim 7, wherein the at least one controller is further configured to:
receive, from the user interface, the one or more light output characteristics for at least one of the plurality of sectors;
drive, by the at least one controller, at least one of plurality of sectors individually at the one or more light output characteristics.

9. The modular light of claim 1, wherein the at least two annular rows of LEDs comprise a first annular row, a second annular row and a third annular row, the first annular row of LEDs are elevationally closer to the light output plane than the second annular row and the third annular row.

10. The modular light of claim 9, wherein the at least one controller is further configured to:
receive, from the user interface, the one or more light output characteristics for at least one of the first, second or third annular rows of LEDs;
drive, by the at least one controller, one of the first, second or third row of the plurality of rows of LEDs at a first light output characteristic; and
drive, by the at least one controller, another of the first, second or third row of the plurality of rows of LEDs at a second light output characteristic which is different than the first light output characteristic.

11. The modular light of claim 1 wherein the power supply interface of the modular light receives curing data from the bio-printing robot end effector.

12. The modular light of claim 1 further including the user interface to receive curing data.

13. The modular light of claim 12 herein the curing data includes LED segment, wavelength information, exposure time, and irradiance.

14. The modular light of claim 13 wherein the LED segment information includes grouping information of the plurality of LEDs, the grouping information defining a plurality of groups of LEDs, each of the plurality of groups having a unique wavelength with respect to the other of the plurality of groups.

15. The modular light of claim 1 wherein the at least one controller includes at least one microprocessor.

16. The modular light of claim 15 herein the at least one microprocessor includes a first microprocessor.

17. A modular light configured to removably attach to a bio-printing robot end effector, comprising:
an annular modular light ring housing with an annular opening configured to receive the end effector of a bio-printing robot, the annular modular light ring housing having a light emitting plate directed outward away from the end effector in the direction of a dispensing tip of the bio-printing robot;
the annular modular light ring housing removably replaceable around the dispensing tip of the bio-printing robot end effector;
a power supply interface to receive electrical power;
the annular modular light ring housing removably replaceable around the dispensing tip of the bio-printing robot end effector and retained in place on the end effector using a coupling;
a plurality of LEDs positioned annularly around the end effector within the annular modular light ring housing, wherein the plurality of LEDs are spaced in at least two annular rows, wherein each of said plurality of at least two annular rows are individually controllable in unique quadrants;
the plurality of light emitting diodes in electrical communication with the power supply interface;
a user interface; and
at least one controller communicatively coupled with the plurality of light emitting diodes and the power supply interface, the at least one controller configured to:
receive, from the user interface, curing data including one or more light output characteristics;
drive a plurality of LEDs defined by LED row information and LED sector information, at a frequency to generate the one or more light output characteristics.

18. The modular light of claim 17, wherein the coupling is a magnet configured to interact with a corresponding magnet of the end effector.

19. The modular light of claim 17, wherein the coupling is a mechanical coupling.

20. The modular light of claim 17, wherein the power supply interface is an electrical contact configured to electrically connect the end effector and the annular modular light ring housing.

21. The modular light of claim 17, wherein the first row of the plurality of LEDs generates light at a first intensity and the second row of the plurality of LEDs generates light a second, differing intensity.

22. The modular light of claim 17, wherein the first and second rows of the plurality of LEDs are each divided into a plurality of sectors, wherein each of the plurality of sectors is separately controlled.

* * * * *